(12) United States Patent
Matsumura et al.

(10) Patent No.: US 12,239,880 B2
(45) Date of Patent: Mar. 4, 2025

(54) SKILL INFORMATION PRESENTATION APPARATUS, SKILL INFORMATION PRESENTATION METHOD, AND PROGRAM

(71) Applicant: NIPPON TELEGRAPH AND TELEPHONE CORPORATION, Tokyo (JP)

(72) Inventors: Seiji Matsumura, Tokyo (JP); Toshitaka Kimura, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 574 days.

(21) Appl. No.: 17/273,725

(22) PCT Filed: Aug. 28, 2019

(86) PCT No.: PCT/JP2019/033605
§ 371 (c)(1),
(2) Date: Mar. 4, 2021

(87) PCT Pub. No.: WO2020/050108
PCT Pub. Date: Mar. 12, 2020

(65) Prior Publication Data
US 2021/0339085 A1    Nov. 4, 2021

(30) Foreign Application Priority Data
Sep. 7, 2018    (JP) .................. 2018-167487

(51) Int. Cl.
*A63B 69/18*    (2006.01)
*A63B 24/00*    (2006.01)
*A63B 71/06*    (2006.01)

(52) U.S. Cl.
CPC .......... *A63B 24/0006* (2013.01); *A63B 69/18* (2013.01); *A63B 71/0622* (2013.01);
(Continued)

(58) Field of Classification Search
None
See application file for complete search history.

(56) References Cited

U.S. PATENT DOCUMENTS 4,906,192 A * 3/1990 Smithard ............... A63B 69/00
                                                          482/901
5,690,591 A * 11/1997 Kenmochi ............. A63B 69/18
                                                            482/9
(Continued)

FOREIGN PATENT DOCUMENTS

CN       106512333 A  *  3/2017
FR          3037816 A1 * 12/2016 ............. A63B 69/18
(Continued)

OTHER PUBLICATIONS

Falda-Buscaiot et al. (2017) "Influence of slope steepness, foot position and turn phase on plantar pressure distribution during giant slalom alpine ski racing," Plos One [online] Accessed on May 4, 2017, website: https://doi.org/10.1371/journal.pone.0176975.
(Continued)

*Primary Examiner* — Shila Jalalzadeh Abyaneh

(57) ABSTRACT

A technology is provided where, in physical exercise performed using plate-shaped equipment, behavior of one's own body and corresponding behavior of equipment can be presented in an intuitively comprehensible manner on the basis of information acquired by a simple device configuration. Information indicating skill relating to a turn in a physical exercise performed by an exerciser performing the physical exercise using plate-shaped equipment is skill information. Included are an equipment behavior information acquiring unit that acquires equipment behavior information, a bodily behavior information acquiring unit that acquires bodily behavior information, and a skill information presenting unit that calculates, from the equipment behavior information and the bodily behavior information, a
(Continued)

first skill indicator/second skill indicator that include information indicating behavior of the equipment/behavior of the body of the exerciser at a start-of-turn time, a middle-of-turn time, and an end-of-turn time, as the skill information, and presents the skill information. The equipment behavior information includes time sequence information of angular velocities relating to a travel direction/an edging direction of the equipment, and the bodily behavior information includes time sequence information of pressure at each region of the soles of the right foot/left foot of the exerciser.

20 Claims, 9 Drawing Sheets

(52) U.S. Cl.
CPC ... *A63B 2071/0625* (2013.01); *A63B 2220/16* (2013.01); *A63B 2220/34* (2013.01); *A63B 2220/62* (2013.01); *A63B 2220/836* (2013.01)

(56) References Cited

U.S. PATENT DOCUMENTS

| | | | | |
|---|---|---|---|---|
| 2005/0038626 | A1* | 2/2005 | Flentov | G01P 15/0891 |
| | | | | 702/141 |
| 2008/0284650 | A1* | 11/2008 | MacIntosh | A63B 24/0021 |
| | | | | 342/357.57 |
| 2013/0093588 | A1* | 4/2013 | Bender | G09B 19/0038 |
| | | | | 340/539.11 |
| 2014/0257744 | A1* | 9/2014 | Lokshin | A61B 5/6813 |
| | | | | 702/141 |
| 2016/0038788 | A1* | 2/2016 | McMillan | A63B 69/0022 |
| | | | | 73/488 |
| 2016/0199693 | A1* | 7/2016 | Vermilyea | A63F 13/211 |
| | | | | 700/91 |
| 2016/0335913 | A1* | 11/2016 | Grant | A61B 5/6807 |
| 2017/0225033 | A1* | 8/2017 | Czaja | A43B 3/34 |
| 2017/0285734 | A1* | 10/2017 | Saito | H04N 13/117 |
| 2017/0312574 | A1* | 11/2017 | Matsuzawa | G16H 20/30 |
| 2018/0055415 | A1* | 3/2018 | Nakao | A61B 5/224 |

FOREIGN PATENT DOCUMENTS

| | | | | |
|---|---|---|---|---|
| JP | 2016000122 | * | 1/2016 | |
| JP | 2016000122 A | * | 1/2016 | |
| JP | 2017522 A | | 1/2017 | |
| JP | 2018099399 A | * | 6/2018 | |
| KR | 20170085869 A | * | 7/2017 | |
| KR | 20180099177 A | * | 9/2018 | |
| WO | WO-2017011814 A1 | * | 1/2017 | A63B 24/0003 |

OTHER PUBLICATIONS

Fasel et al. (2017) "An Inertial Sensor-Based Method for Estimating the Athlete's Relative Joint Center Positions and Center of Mass Kinematics in Alpine Ski Racing," Frontiers in Physiology, vol. 8, Article 350, pp. 1-12.
Matsumura et al. (2018) "Comfortable Measurement of Ski-turn Skill using Inertial and Plantar-pressure Sensors," CSPORTS 2018—6th International Congress on Sport Sciences Research and Technology Support, pp. 145-148.

* cited by examiner (a) X axis in the intermediate skier (b) Y axis in the intermediate skier (c) Z axis in the intermediate skier (a) X axis in the expert skier (b) Y axis in the expert skier (c) Z axis in the expert skier

SKILL INFORMATION PRESENTATION APPARATUS, SKILL INFORMATION PRESENTATION METHOD, AND PROGRAM

CROSS-REFERENCE TO RELATED APPLICATIONS

This application is a U.S. 371 Application of International Patent Application No. PCT/JP2019/033605, filed on 28 Aug. 2019, which application claims priority to and the benefit of JP Application No. 2018-167487, filed on 7 Sep. 2018, the disclosures of which are hereby incorporated herein by reference in their entireties.

TECHNICAL FIELD

The present invention relates to technology for presenting skill information in a sport where plate-shaped equipment is operated by adjusting the way in which force is applied, such as in skiing, for example.

BACKGROUND ART

In order to improve skill in a sport, there is a need to compare and comprehend how behavior of one's own body and corresponding behavior of equipment differs from targeted behavior.

NPL 1 discloses technology to measure plantar pressure distribution of an alpine skier skiing down a giant slalom competition course, using plantar pressure sensors, and display measurement values as a graph.

Also, NPL 2 discloses technology of estimating and visualizing bodily behavior (kinematics) while skiing, using a great number of inertial sensors attached to the entire body.

CITATION LIST

Non Patent Literature

[NPL 1] Thomas Falda-Buscaiot, Frederique Hintzy, Patrice Rougier, Patrick Lacouture, Nicolas Coulmy, "Influence of slope steepness, foot position and turn phase on plantar pressure distribution during giant slalom alpine ski racing",
PLoS ONE 12(5): e0176975,
https://doi.org/10.1371/journal.pone.0176975, 2017.
[NPL 2] Benedikt Fasel, Jorg Sporri, Pascal Schutz, Silvio Lorenzetti and Kamiar Aminian, "An Inertial Sensor-Based Method for Estimating the Athlete's Relative Joint Center Positions and Center of Mass Kinematics in Alpine Ski Racing",
Front Physiol. 2017; 8: 850,
https://doi.org/10.3389/fphys.2017.00850, 2017.

SUMMARY OF THE INVENTION

Technical Problem

In order to achieve a high level of performance in sports where plate-shaped equipment is operated by adjusting the way in which force is applied to the equipment, such as skiing, snowboarding, grass skiing, surfing, and windsurfing, there is a need to comprehend the relation between the behavior of one's own body and the corresponding behavior of the equipment, and learn how the body should be moved to bring the behavior of the equipment closer to ideal behavior of the equipment.

In NPL 1 and NPL 2, one's own bodily behavior can be comprehended, but it is difficult to comprehend how that affects the behavior of the skis. Also, NPL 2 has a problem in that a great number of inertial sensors and dedicated software to perform complicated analysis are necessary, and accordingly facilities are too large in scale and costly for common skiers to use.

Accordingly, it is an object of the present invention to provide a technology where, in physical exercise using plate-shaped equipment, behavior of one's own body and corresponding behavior of equipment are presented in a manner that can be intuitively comprehended on the basis of information acquired by a simple device configuration.

Means for Solving the Problem

An aspect of the present invention is a skill information presenting device, where information indicating skill relating to a turn in a physical exercise performed by an exerciser performing the physical exercise using plate-shaped equipment is skill information. The skill information presenting device includes an equipment behavior information acquiring unit that acquires equipment behavior information indicating behavior of the equipment, a bodily behavior information acquiring unit that acquires bodily behavior information indicating behavior of the body of the exerciser and a skill information presenting unit that calculates, from the equipment behavior information and the bodily behavior information, a first skill indicator that includes information indicating behavior of the equipment at a start-of-turn time, a middle-of-turn time, and an end-of-turn time, and a second skill indicator that includes information indicating behavior of the body of the exerciser at the start-of-turn time, the middle-of-turn time, and the end-of-turn time, as the skill information, and presents the skill information. The equipment behavior information includes time sequence information regarding angular velocity relating to a travel direction of the equipment and angular velocity relating to an edging direction of the equipment, and the bodily behavior information includes time sequence information of pressure at each region of the sole of the right foot of the exerciser and pressure at each region of the sole of the left foot of the exerciser.

Effects of the Invention

According to the present invention, in physical exercise using plate-shaped equipment, behavior of one's own body and corresponding behavior of equipment can be presented in a manner that can be intuitively comprehended on the basis of information acquired by a simple device configuration.

DESCRIPTION OF EMBODIMENTS

An embodiment of the present invention will be described in detail below. Note that components having the same function are denoted by the same numbers, and redundant description will be omitted.

Technical Background

Exercise that is the object of the embodiment of the present invention is sports where plate-shaped equipment is operated by adjusting the way in which force is applied to the equipment, such as skiing, snowboarding, grass skiing, surfing, and windsurfing.

There are methods of measuring and presenting skills in exercise, taking into consideration the relation of the exercising state of the bodily parts of an exerciser such as muscle activity and so forth, the mental state of the exerciser, and the performance of equipment, for example. However, it is an object of the embodiment of the present invention to provide a skill information presenting technology that is easily intuitively comprehended even by novices and is readily introduced, by presenting information that contributes to improvement of skills regarding an objective exercise in a simple manner, on the basis of information acquired by a simple device configuration. Particularly, it is an object to focus on the two of (1) output of exercise by the exerciser as to the equipment, and (2) behavior of the equipment that is manifested as a result thereof, and to present the relation therebetween in an intuitively comprehendible form.

Experiment results serving as a background for the embodiment of the present invention will be described below.

Experiment Results Serving as Background

Figure 1:
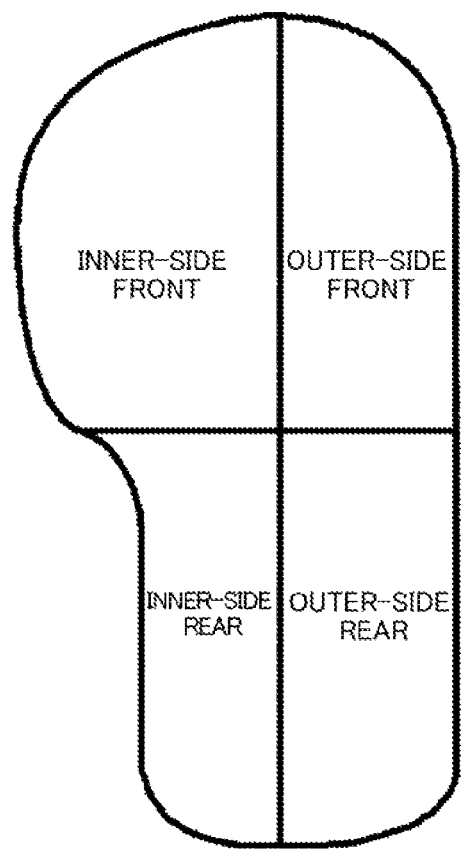
FIG. 1 is a diagram illustrating an example of regions of the sole of a right foot.

In experiments, equipment behavior information and bodily behavior information during turning (turning action) were measured with sensors and acquired, for advanced (Expert skier) and intermediate (Intermediate skier) skiers. For equipment behavior, one inertial sensor was attached near the binding on each of two skis, and angular velocity was measured in the X axis, Y axis, and Z axis directions. The angular velocity in the X axis direction here is the velocity of the ski turning in a perpendicular direction as to the snow surface, the angular velocity in the Y axis direction is the velocity of the ski turning in the edging direction, and the angular velocity in the Z axis direction is the velocity of the ski turning in a lateral direction as to the snow surface. Also, regarding bodily behavior, plantar pressure sensors were attached to the insoles of ski boots, and pressure of the soles of the feet was measured. Specifically, the soles of each of the right foot and the left foot were divided into the four regions of (1) inner-side front (MF: Medial Forefoot), (2) outer-side front (LF: Lateral Forefoot), (3) inner-side rear (MH: Medial Heel), and (4) outer-side rear (LH: Lateral Heel), and average values of pressure were measured in each region. FIG. 1 illustrates the regions of the sole of the right foot.

Figure 2:
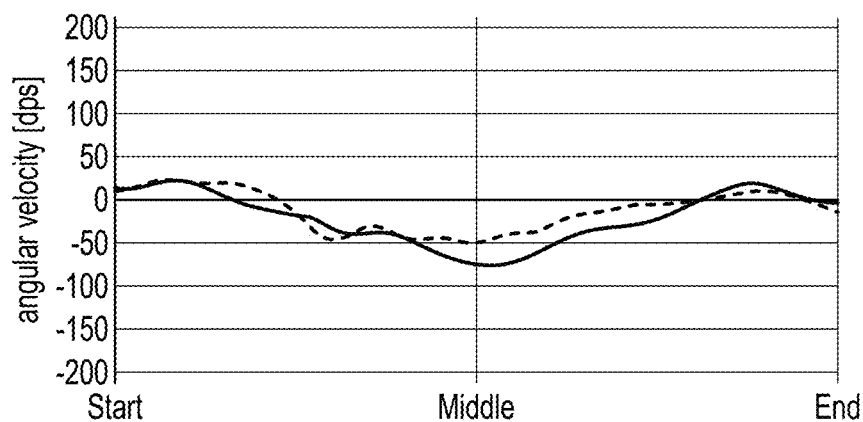
FIG. 2 is a diagram illustrating an example of temporal change in angular velocity in each axial direction.
Figure 2:
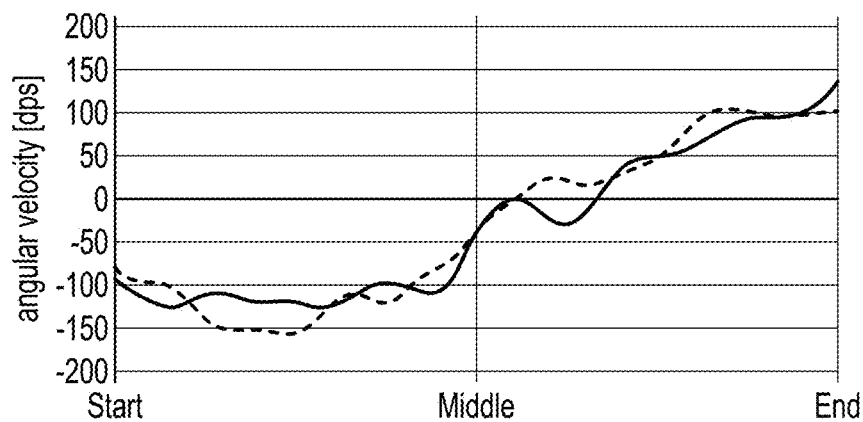
Figure 2:
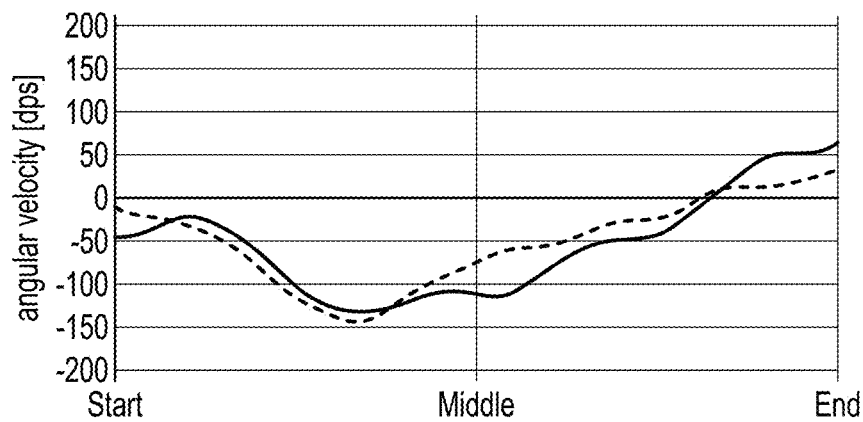
Figure 3:
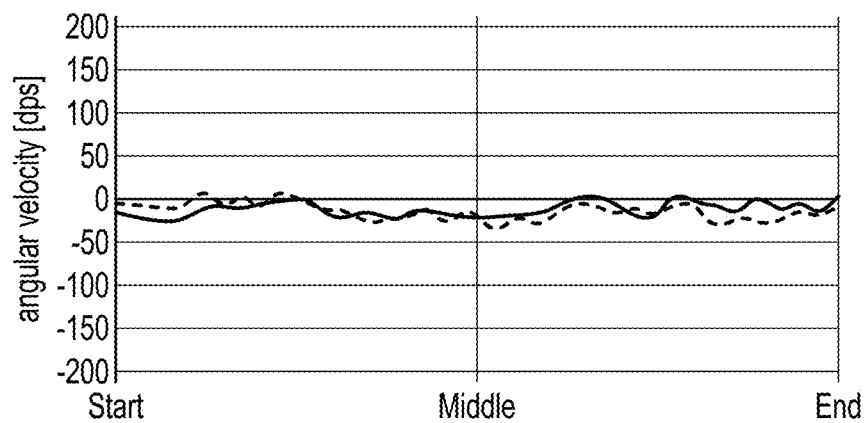
FIG. 3 is a diagram illustrating an example of temporal change in angular velocity in each axial direction.
Figure 3:
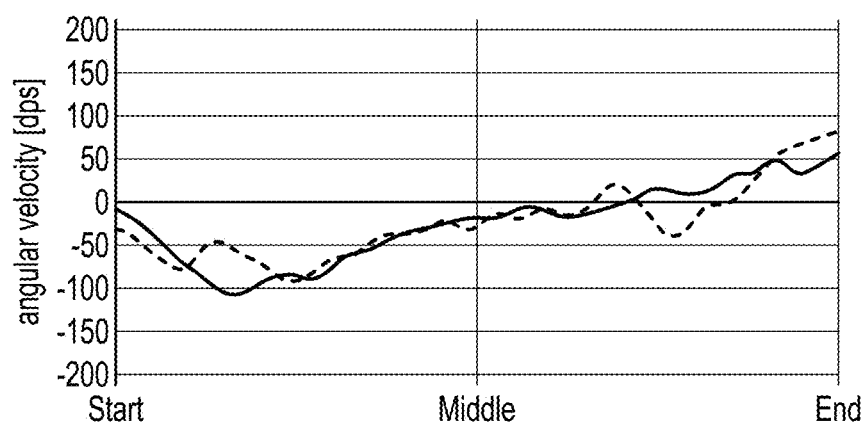
Figure 3:
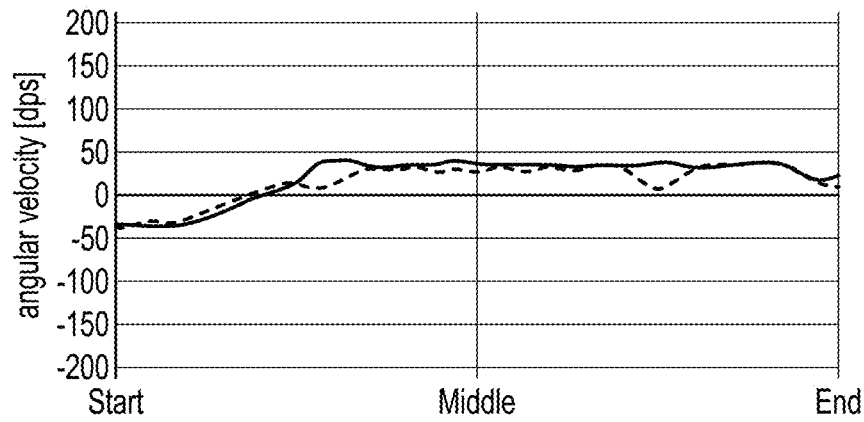

First, behavior information of the equipment will be described. FIG. 2 and FIG. 3 illustrate temporal change of angular velocity in each axis direction acquired by experimentation. FIGS. 2(*a*), (*b*), and (*c*) illustrate data of angular velocity (in increments of dps (degree per second)) acquired from an intermediate skier, and FIGS. 3(*a*), (*b*), and (*c*) illustrate angular velocity acquired from an expert skier, showing the angular velocity in the X axis, Y axis, and Z axis directions in order from the top. From the results of the X axis direction, it can be seen that the change in the angular velocity is greater for the intermediate skier than the expert skier. This means that chattering in the up-down direction of the skis is greater for the intermediate skier than the expert skier. From the results of the Y axis direction, it can be seen that the change in angular velocity in the edging direction near the middle of the turn is smaller for the expert skier as compared to the intermediate skier. This means that the more an expert the skier is, there is a section near the turnback portion of the turn where the edging angle is temporarily stable. From the results of the Z axis direction, it can be seen that the expert skier has less change in angular velocity through the entire turn, as compared to the intermediate skier, and also the expert skier has a section near the middle of the turn where the angular velocity is approximately constant. The difference between the intermediate skier and the expert skier particularly is easily seen regarding change in angular velocity relating to the Y axis direction (edging direction of the skis) and Z axis direction (direction of travel of the skis). Accordingly, it is conceivable that behavior information of skis that has a high level of correlation with the level of skill in skiing technique can be comprehended by using data acquired relating to at least these two axial directions.

Figure 4:
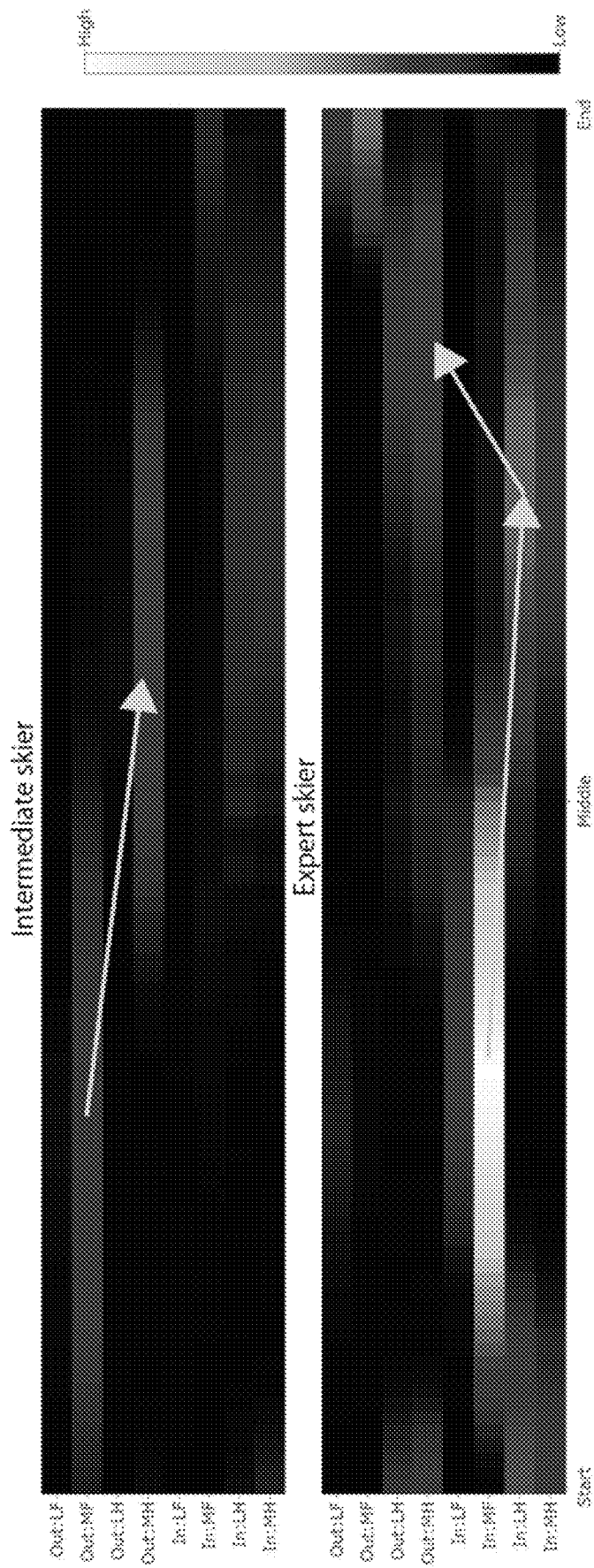
FIG. 4 is a diagram illustrating an example of temporal change of pressure in regions of the soles of both feet.

Next, behavior information of the body will be described. FIG. 4 illustrates temporal change of pressure at the four regions of the soles of the feet for the inside leg (In) and the outside leg (Out). The higher the color density is, the lower the pressure indicated is. The upper diagram (FIG. 4(*a*)) is of an intermediate skier, and the lower diagram. (FIG. 4(*b*)) is of an expert skier. From these results, the way in which the expert skier places the most force on the inner-side front of the inside leg (In: MF) from the start of the turn to the middle of the turn, and thereafter shifts the region with the greatest force applied to the outer-side rear of the inside leg (In: LH) and then to the inner-side front of the outside leg (Out: MF) toward the end of the turn, can be seen. Conversely, the intermediate skier has the greatest pressure at the inner-side front of the outside leg (Out: MF) from the start of the turn to the middle of the turn, and the region where pressure is high shifts to the inner-side rear of the outside leg (Out: MH) from the middle of the turn to the end of the turn. That is to say, it can be seen that the intermediate skier is not as adept in using the inside leg and outside leg separately according to the situation as the expert skier. Accordingly, it is thought that the difference in bodily behavior between the expert skier and the intermediate skier can be comprehended by d ding the foot sole of each of the inside leg and the outside leg into four regions, and observing the temporal transition of regions where pressure is high.

First Embodiment

A skill information presenting device 100 presents information indicating skill (hereinafter referred to as skill information) regarding turning (turning action) of physical exercise of an exerciser performing the physical exercise using plate-shaped equipment.

Figure 5:
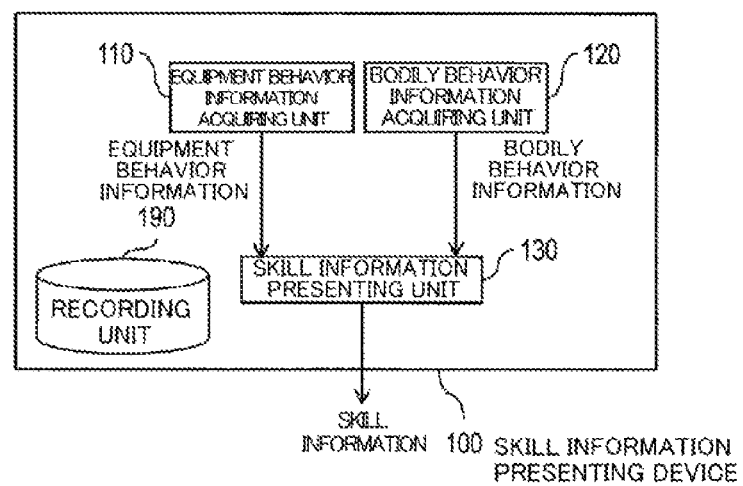
FIG. 5 is a block diagram illustrating an example of a configuration of a skill information presenting device 100.
Figure 6:
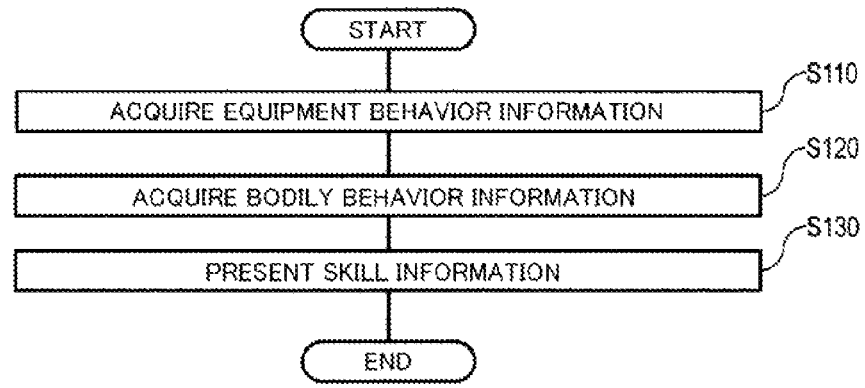
FIG. 6 is a flowchart illustrating an example of operations of the skill information presenting device 100.

The skill information presenting device 100 will be described below with reference to FIG. 5 and FIG. 6. FIG. 5 is a block diagram illustrating a configuration of the skill information presenting device 100. FIG. 6 is a flowchart illustrating operations of the skill information presenting device 100. The skill information presenting device 100 includes an equipment behavior information acquiring unit 110, a bodily behavior information acquiring unit 120, a skill information presenting unit 130, and a recording unit 190, as illustrated in FIG. 5. The recording unit 190 is a component that records, as appropriate, information necessary for processing by the skill information presenting device 100.

Operations of the skill information presenting device 100 will be described following FIG. 6.

Equipment Behavior Information Acquiring Unit 110

In S110, the equipment behavior information acquiring unit 110 acquires and outputs equipment behavior information indicating behavior of the equipment such as a ski, snowboard, or the like, using a sensor attached to the equipment. The equipment behavior information includes time sequence information of angular velocity relating to the direction of travel of the equipment (Z axis direction) and angular velocity relating to the edging direction of the equipment (Y axis direction). The equipment behavior information may include time sequence information of angular velocity relating to the up-down direction (X axis direction) of the equipment, in addition to the time sequence information of these two angular velocities.

Inertial sensors, for example, can be used for measuring angular velocity. In a case of skis, one inertial sensor can be attached to each of the two skis, at the upper face (binding side) thereof. In the case of a snowboard, a surfboard, or a sailboard, one or two inertial sensors can be attached to the upper face of the board, around the middle.

Note that while the number of sensors attached is not limited to the above, a minimal number is preferable, since the object is to comprehend behavior with a simple device configuration. Also, the positions of attaching the sensor are not limited to the above examples, but the sensor is preferably attached nearby (close) to a portion where the body of the exerciser comes into contact with the equipment, for example.

Bodily Behavior Information Acquiring Unit 120

In S120, the bodily behavior information acquiring unit 120 acquires and outputs bodily behavior information indicating the behavior of the body of the exerciser, using the sensors. The bodily behavior information includes time sequence information of pressure on a face where the body of the exerciser and the equipment come into contact.

A plantar pressure sensor, for example, can be used for measurement of pressure. In a case of skis, a snowboard, or grass skis, plantar pressure sensors are attached to the insoles of the boots, to measure pressure of the soles of the feet. The soles of both feet are divided into the four regions of (1) inner-side front, (2) outer-side front, (3) inner-side rear, and (4) outer-side rear, for example, and the pressure in each region is measured. Note that one or more plantar pressure sensors may be attached to each region, or one plantar pressure sensor that can measure pressure of the entire foot sole may be attached, to measure pressure in each region. In a case of a surfboard or a sailboard, plantar pressure sensors can be attached to insoles of surf booties, for example, to perform measurement.

Note that in a case where a plurality of measurement values regarding pressure is acquired in each region, a representative value (e.g., average value) may be used for the pressure in each region.

Accordingly, in a case of measuring pressure at the soles of the feet during turning in the physical exercise, the bodily behavior information includes time sequence information of pressure at each region of the sole of the right foot of the exerciser and pressure at each region of the sole of the left foot of the exerciser.

Skill Information Presenting Unit 130

In S130, the skill information presenting unit 130 calculates and presents a first skill indicator including information indicating the behavior of the equipment at a start-of-turn time, a middle-of-turn time, and an end-of-turn time, and a second skill indicator including information indicating the behavior of the body of the exerciser at the start-of-turn time, middle-of-turn time, and end-of-turn time, as skill information, from the equipment behavior information acquired in S110 and the bodily behavior information acquired in S120. That is to say, the skill information is information that shows the behavior of the equipment and the body of the exerciser at the start-of-turn time, middle-of-turn time, and end-of-turn time. Now, start-of-turn time is the time at which a turn starts, middle-of-turn time is the time midway through the turn, and end-of-turn time is the time at which the turn ends.

The times of the start of turn, middle of turn, and end of turn may be detected using the equipment behavior information, or may be detecting by a method such as analyzing video acquired separately or the like. An example of procedures of detecting the times using the equipment behavior information will be described below.

First, out of the equipment behavior information, the skill information presenting unit 130 uses the time sequence information of angular velocity relating to the direction of travel of the equipment to determine the type of turn, and generates determination results of the turn type. The turn type here is a sideslip turn (skid turn) or carving turn. Specifically, the skill information presenting unit 130 determines that, in a case where vibration in the direction of travel (i.e., amplitude of angular velocity in a predetermined time segment) is great, the turn type is a sideslip turn, and otherwise the turn type is a carving turn. Note that whether the vibration in the direction of travel is great or not can be determined by whether the vibration is no less than predetermined threshold value or not (or exceeds a predetermined threshold value or not), for example.

Next, the skill information presenting unit 130 detects the start-of-turn time using the equipment behavior information, in accordance with the determination results of the turn type. Specifically, in a case where the turn type is a sideslip turn, the skill information presenting unit 130 detects a time at which the value of angular velocity relating to the edging direction of the equipment is smallest (or greatest) as the start-of-turn time. Also, in a case where the turn type is a carving turn, the skill information presenting unit 130 detects a change point from an immediately preceding time segment where the value of angular velocity relating to the travel direction of the equipment is constant, i.e., a time at which the value of angular velocity begins to increase or decrease, as the start-of-turn time. This will be described by way of FIG. 3(c). The segment where the value of the Z axis maintains around −50 degrees corresponds to the immediately-preceding turn, and the value of angular velocity begins to increase from −50 degrees toward 50 degrees at the start time of the next turn (i.e., the turn of which the start-of-turn time is the object of detection). This time at which the increase starts is the start-of-turn time.

Note that, since turn actions are performed alternately left and right, whether the angular velocity is positive or negative in each turn is decided depending on which of change in left and right turns is set to positive for the Y axis and Z axis. In the example in FIG. 3(c), the value of angular velocity of the turn that is the object of detection is set to positive, so the start-of-turn time is the time at which the value of angular velocity begins to increase, but in a case where the value of angular velocity of the turn that is the object of detection is set to negative, the start-of-turn time will be the time at which the value of angular velocity begins to decrease.

The skill information presenting unit 130 also detects the middle-of-turn time using the equipment behavior information, in accordance with the determination results of the turn type. Specifically, in a case where the turn type is a sideslip turn, the skill information presenting unit 130 detects the time at which the value of angular velocity relating to the edging direction of the equipment becomes 0, as the middle-of-turn time. Also, in a case where the turn type is a carving turn, the skill information presenting unit 130 detects, out of a time segment where the value of angular velocity relating to the travel direction of the equipment is constant (a time segment where a derivative value of angular velocity is 0, for example), a time at which the value of angular velocity relating to the edging direction of the equipment becomes 0, as the middle-of-turn time.

The skill information presenting unit 130 repeats the above-described processing in order from the beginning of the equipment behavior information, and detects one or more of each of the start-of-turn time and middle-of-turn time. Note that the end-of-turn time may be the same as the next start-of-turn time.

Figure 7:
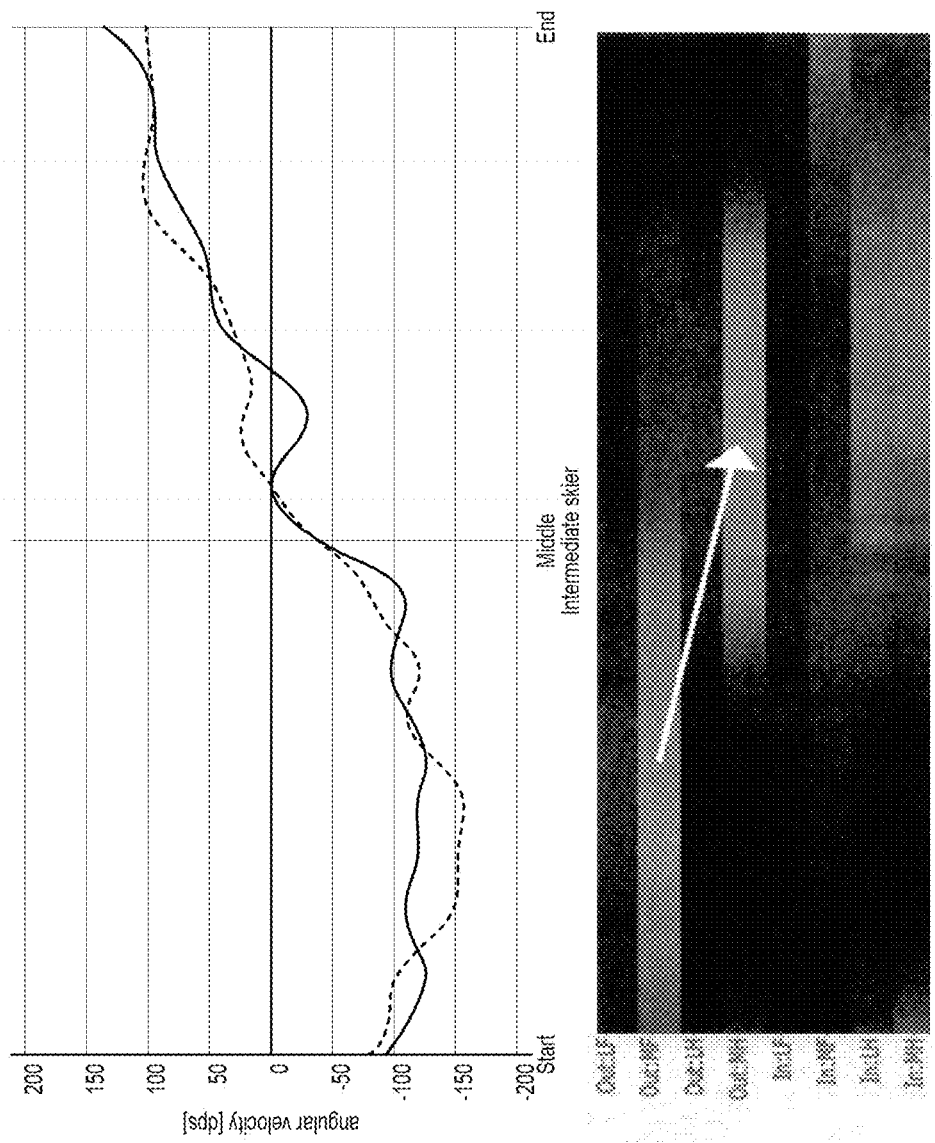
FIG. 7 is a diagram illustrating an example of skill information presented by the skill information presenting device 100.

A skill information presentation method will be described below. The skill information presenting unit 130 presents a first skill indicator as a diagram illustrating temporal change in the two angular velocities (angular velocity relating to travel direction and edging direction) in a segment from start-of-turn time to end-of-turn time, for each turn (i.e., unit of exercise). This may be presented as graphs, such as illustrated in FIG. 2 and FIG. 3, for example. The skill information presenting unit 130 also presents a second skill indicator as a diagram illustrating temporal change in pressure at each region of the two soles of the feet in a segment from start-of-turn time to end-of-turn time for each turn. This may be presented as a diagram where temporal change in pressure in each region is visualized so that magnitude of pressure and color density correspond, such as illustrated in FIG. 4, for example. Note that visualization is made in FIG. 4 so that the greater the pressure is, the lighter the color is. Also, an arrangement may be made where the temporal scales of the diagram illustrating the first skill indicator and the diagram illustrating the second skill indicator are aligned and presented side by side as in FIG. 7, to facilitate understanding of the correlation between equipment behavior and bodily behavior.

Figure 8:
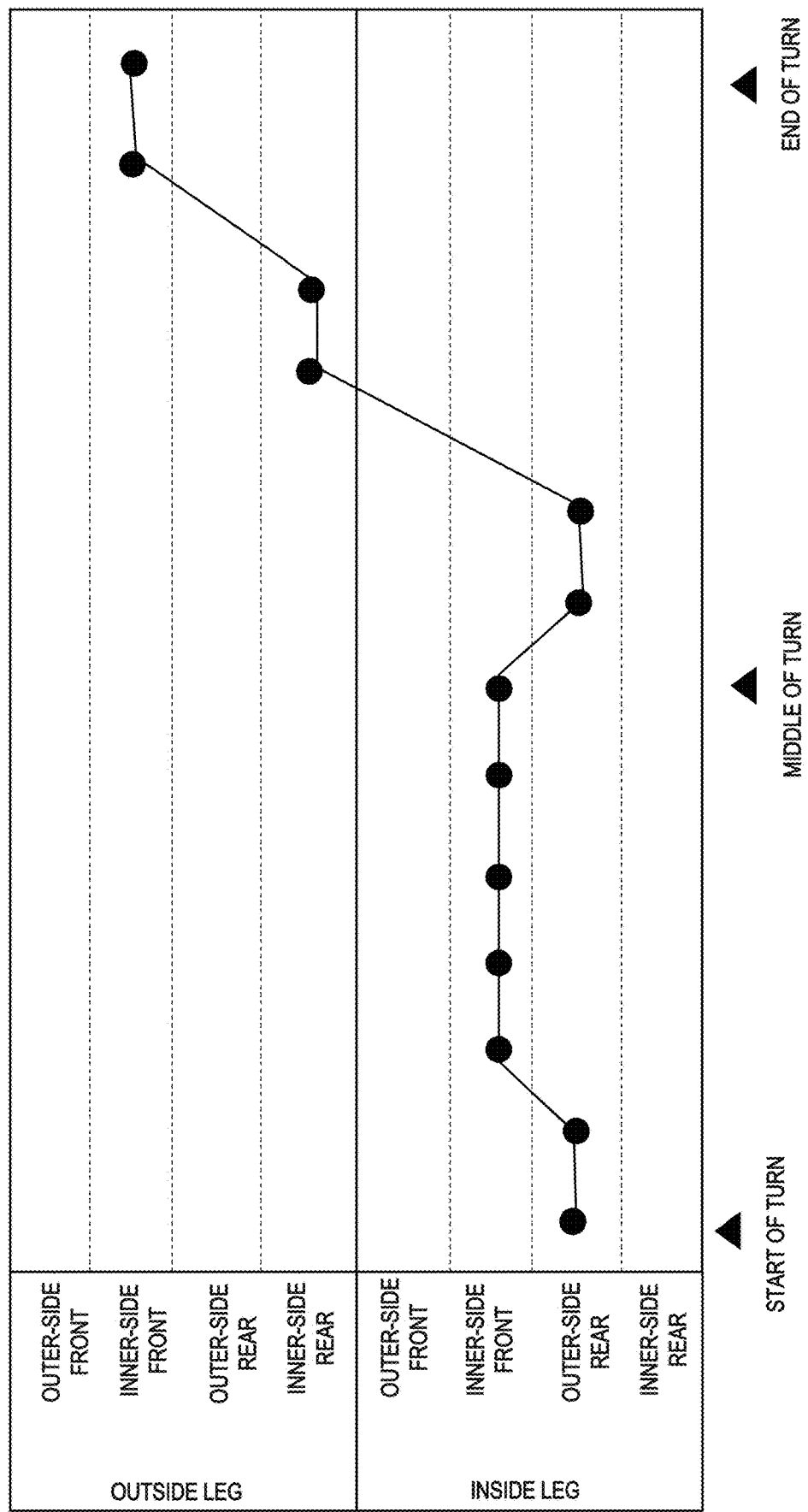
FIG. 8 is a diagram illustrating an example of skill information presented by the skill information presenting device 100.

As a different method, the skill information presenting unit 130 may present the second skill indicator as a diagram illustrating temporal change in a region where the pressure is the greatest out of the regions of the two soles of the feet in a segment from start-of-turn time to end-of-turn time for each turn. For example, this may be presented as a line graph where the region where the pressure is the highest at each time is plotted, as in FIG. 8. Thus, the temporal transition of pressure among the regions is visualized.

Figure 9:
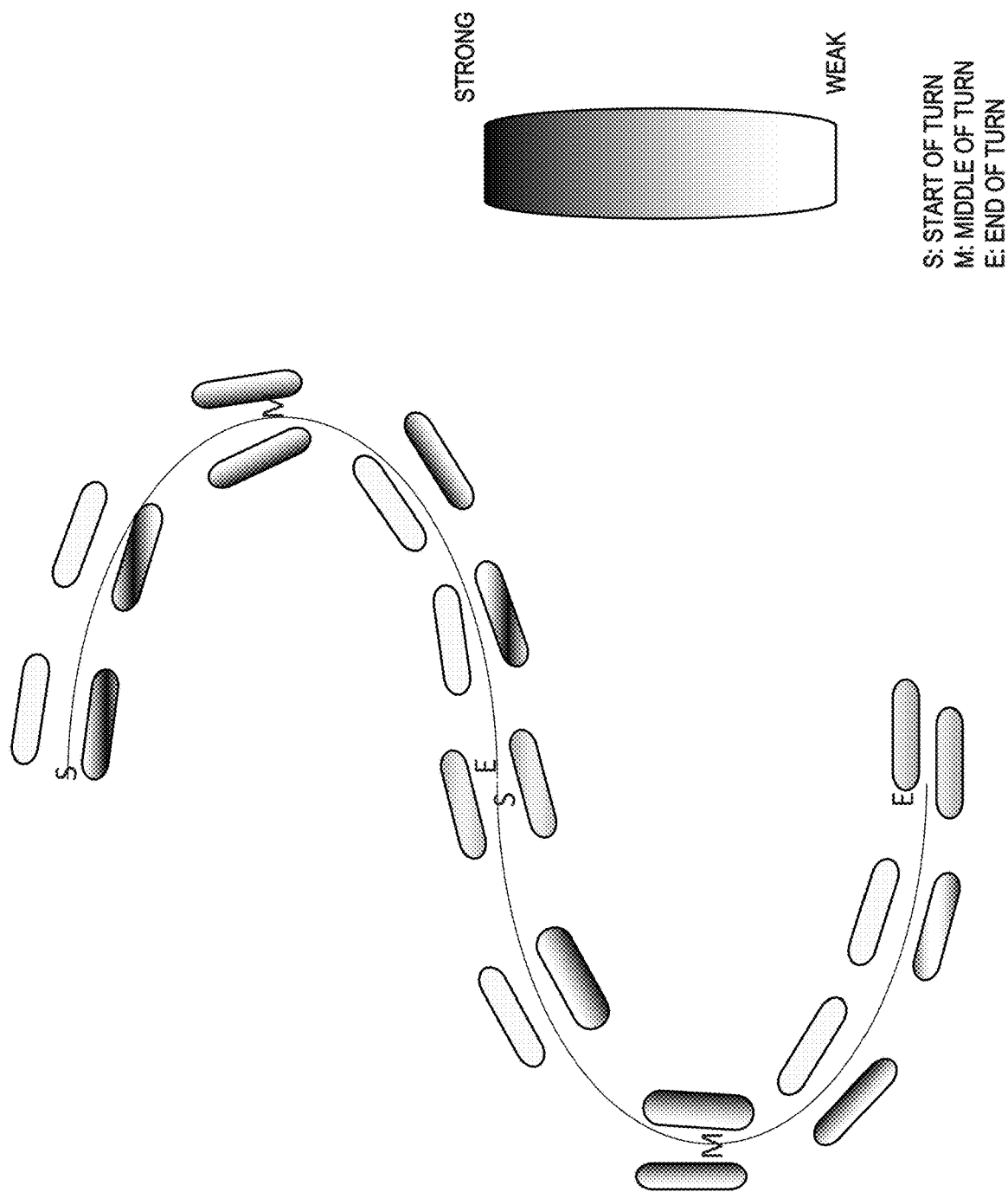
FIG. 9 is a diagram illustrating an example of skill information presented by the skill information presenting device 100.

Further, as a different method, the skill information presenting unit 130 may present the first skill indicator as a diagram displaying the two angular velocities (angular velocities relating to travel direction and edging direction) superimposed on a diagram representing turn paths. At this time, for the angular velocity relating to the travel direction of equipment, the orientation of the travel direction of the equipment calculated from this angular velocity is displayed as an angle as to the path, and for the angular velocity relating to the edging direction of the equipment, the inclination as to the face of contact with the equipment calculated from this angular velocity is displayed by color. For example, this may be presented as a diagram superimposed on a diagram representing turn paths, as in FIG. 9. In this example, this indicates that the equipment is inclined toward the direction with higher color density (i.e., the higher the color density is, the more the equipment is inclined in a direction so as to be closer to the face of contact of the equipment (e.g., snow surface)). Alternatively, a video where the two angular velocities are superimposed on turn paths so as to be visualized may be used for presentation.

Modification 1

Although the skill information presenting unit 130 has been described as visually presenting skill information using diagrams, an arrangement may be made where this is presented auditorily using sound.

The skill information presenting device 100 that presents skill information using sound will be described below. The recording unit 190 has recorded therein beforehand sounds of mutually different frequencies or tones, assigned to the angular velocity relating to the travel direction of the equipment and the angular velocity relating to the edging direction of the equipment. For example, in a case where the physical exercise being performed is skiing using plate-shaped equipment, two skis, which are the equipment, are used, so four different sounds are recorded. In a case where the physical exercise is snowboarding, there is only one board used as the equipment, so two different sounds are recorded. The recording unit 190 also records beforehand sounds of mutually different frequencies or tones assigned to each region of the sole of the right foot of the exerciser and each region of the sole of the left foot of the exerciser. In a case where the soles of both the left and right feet are each divided into four regions, for example, eight different sounds are recorded.

The skill information presenting unit 130 uses time sequence information of angular velocity relating to travel direction of the equipment and angular velocity relating to the edging direction of the equipment in an ideal turn, and time sequence information of the two angular velocities included in the equipment behavior information acquired in S110, to calculate time sequence information of difference between the two angular velocities and the ideal turn. The skill information presenting unit 130 further uses this time sequence information of difference to sequentially reproduce the sounds recorded in the recording unit 190 that are assigned to the two angular velocities such that the smaller the difference, is the smaller the volume is (or the greater the difference is, the larger the volume is), thereby presenting the first skill indicator. The time sequence information of angular velocity relating to travel direction of the equipment and angular velocity relating to the edging direction of the equipment in an ideal turn here is, for example, time sequence information of angular velocity relating to travel direction of the equipment and angular velocity relating to the edging direction of the equipment in a turn performed by an expert skier, and is recorded in the recording unit 190 beforehand. Note that hereinafter, time sequence information of angular velocity relating to travel direction of the equipment in an ideal turn will be referred to as first target time sequence information, and time sequence information of angular velocity relating to the edging direction of the equipment in an ideal turn will be referred to as second target time sequence information. The skill information presenting unit 130 may reproduce the sounds assigned to the two angular velocities, at the volumes corresponding to the respective differences, at the same time. According to this arrangement, presentation is made such that the closer the turn by the exerciser is to the ideal turn, the smaller the feedback reproduction sound to the exerciser is.

Note that instead of the volume being smaller the smaller the difference is, an arrangement may be made where when the difference is smaller than (no greater than) a predetermined threshold value, a sound indicating an ideal turn is reproduced, and otherwise, a sound that differs from the sound indicating an ideal turn is reproduced (alternatively, no sound (an inaudibly small sound) is reproduced).

Also, it is needless to say that a configuration may be made where only part of the information of the calculated time sequence information of difference is presented as sound, instead of a configuration where all included information is presented as sound. For example, a configuration may be made where only a predetermined number is selected with priority from those with a great difference and presented as sound.

The skill information presenting unit 130 uses the time sequence information of pressure in each region of the two feet soles included in the bodily behavior information acquired in S120 to calculate the time sequence information of the region where the pressure is the highest out of the regions of the two feet soles. Further, the skill information presenting unit 130 uses the times sequence information of the region where the pressure is the highest to sequentially reproduce sound assigned to the region where the pressure is the highest at each time, thereby presenting the second skill indicator. Thus, the exerciser can comprehend regions where his/her own weight is being placed in real time. This can also be used as feedback that prompts improvement in skill by adjusting and correcting the way force is applied, so as to be closer to the sound when an ideal pressure transition is performed.

Note that an arrangement may be made where sounds are assigned to each region of the soles (e.g., a total of eight regions, of four regions for the sole of the right foot and four regions for the sole of the left foot) such that the sounds corresponding to temporal change of pressure in an ideal turn by an expert skier make up a melody, and recorded in the recording unit 190. According to this arrangement, feedback can conceivably be made that is more effective, since the exerciser can easily understand the sounds for an ideal turn.

Alternatively, the skill information presenting unit 130 uses time sequence information of pressure in each region of the two feet soles in an ideal turn, and time sequence information of pressure in each region of the two feet soles included in the bodily behavior information acquired in S120, to calculate time sequence information of difference between the pressure in each region and in the ideal turn. The skill information presenting unit 130 further uses this time sequence information of difference to sequentially reproduce the sounds recorded in the recording unit 190 that are assigned to pressure in each region such that the smaller the difference is the smaller the volume is (or the greater the difference is the larger the volume is), thereby presenting the second skill indicator. The time sequence information of pressure at each region of the two soles of the feet in an ideal turn here is, for example, time sequence information of pressure at each region of the two soles of the feet in a turn performed by an expert skier, and is recorded in the recording unit 190 beforehand. Note that hereinafter, time sequence information of pressure at each region of the two soles of the feet in an ideal turn will be referred to as third target time sequence information. Also, the skill information presenting unit 130 may reproduce the sounds assigned to the pressure at each region, at the volumes corresponding to the respective differences, at the same time. According to this arrangement, presentation is made so that the closer the turn by the exerciser is to the ideal turn, the smaller the feedback reproduction sound to the exerciser is.

Note that instead of the volume being smaller the smaller the difference is, an arrangement may be made where when the difference is smaller than (no greater than) a predetermined threshold value, a sound indicating an ideal turn is reproduced, and otherwise, a sound that differs from the sound indicating an ideal turn is reproduced (alternatively, no sound (an inaudibly small sound) is reproduced).

Also, it is needless to say that a configuration may be made where only part of information of the calculated time sequence information of difference is presented as sound, instead of a configuration where all included information is presented as sound. For example, a configuration may be made where only a predetermined number is selected with priority from those with a great difference and presented as sound.

To summarize the above, the skill information presenting unit 130 uses the time sequence information of the two angular velocities to identify a sound to reproduce out of sounds assigned to the two angular velocities, and sequentially reproduces the identified sound, thereby presenting the first skill indicator. Further, the skill information presenting unit 130 uses the time sequence information of pressure at each region of the two soles of the feet to identify a sound to reproduce out of sounds assigned to the regions, and sequentially reproduces the identified sound, thereby presenting the second skill indicator.

In particular, the skill information presenting unit 130 identifies sounds to reproduce on the basis of the difference regarding time sequence information of difference between the first target time sequence information and the time sequence information of the angular velocity relating to the travel direction of the equipment included in the equipment behavior information acquired in S110, and time sequence information of difference between the second target time sequence information and the time sequence information of the angular velocity relating to the edging direction of the equipment included in the equipment behavior information acquired in S110. Further, the skill information presenting unit 130 sequentially reproduces these identified sounds such that the smaller the difference is, the smaller the volume is, thereby presenting the first skill indicator. Further, the skill information presenting unit 130 identifies the sound to reproduce on the basis of the difference regarding time sequence information of difference between the third target time sequence information and the time sequence information of the pressure at each region of the two soles of the feet included in the bodily behavior information acquired in S120. Further, the skill information presenting unit 130 sequentially reproduces the identified sounds, such that the smaller the difference is the smaller the volume is, thereby presenting the second skill indicator. Now, the sound identified as the sound to be reproduced includes no sound (an inaudibly small sound). Accordingly, this includes a case of presenting only part of the information in the time sequence information of difference that has been calculated, as sound.

As described above, in a case of using sound to present skill information, listening while exercising is enabled, thereby overcoming the shortcoming of using diagrams for visual information or the like, which is that viewing during exercising cannot be performed.

Modification 2

The bodily behavior information acquiring unit 120 may further acquire time sequence information of a center-of-gravity position of the right foot of the exerciser and of a center-of-gravity position of the left foot of the exerciser, as bodily behavior information.

In this case, the skill information presenting unit 130 presents the second skill indicator as a diagram or video showing temporal change in the two center-of-gravity positions. For example, in a case of presenting as a diagram superimposed on a diagram illustrating turn paths as in FIG. 9, the center-of-gravity position at a time corresponding to an icon representing the equipment (the skis) can be presented superimposed. Presentation may also be made visualized so temporal change of the center-of-gravity positions in a region of the right foot and a region of the left foot at each time can be easily understood.

Alternatively, the skill information presenting unit 130 uses time sequence information of the center-of-gravity position of the right foot and the center-of-gravity position of the left foot in an ideal turn, and time sequence information of the two center-of-gravity positions included in the bodily behavior information acquired in S120, to calculate time sequence information of difference between the two center-of-gravity positions and the ideal turn. The skill information presenting unit 130 further uses this time sequence information of difference to sequentially reproduce the sounds recorded in the recording unit 190 that are assigned to the two center-of-gravity positions such that the smaller the difference is the smaller the volume is (or the greater the difference is the larger the volume is), thereby presenting the second skill indicator. Note that the recording unit 190 stores sounds of frequencies or tones that are different from each other, assigned to the right foot and the left foot beforehand. The skill information presenting unit 130 may reproduce the sounds assigned to the two center-of-gravity positions (i.e., two different sounds) at the same time at volumes corresponding to the respective differences.

According to the invention of the present embodiment, in physical exercise using plate-shaped equipment, behavior of one's own body and corresponding behavior of equipment can be presented in an intuitively comprehensible manner on the basis of information acquired by a simple device configuration.

NOTES

The device according to the present invention may be, as a singular hardware entity for example, provided with an input unit to which a keyboard or the like is connectable, an output unit to which a liquid crystal display or the like is connectable, a communication unit to which a communication device (e.g., communication cable) capable of externally communicating from the hardware entity is connectable, a CPU (Central Processing Unit, may be provided with cache memory, a register, or the like), RAM and ROM which are memory, an external storage device that is a hard disk, and a bus that connects the input unit, output unit, communication unit, CPU, RAM, ROM, and external storage device, so that exchange of data can be performed therebetween. Also, a device (drive) that can read and write from and to a recording medium such as a CD-ROM may be provided to the hardware entity as necessary. Examples of a physical entity provided with such hardware resources include a general-purpose computer and the like.

The external storage device of the hardware entity stores programs necessary for realizing the above-described functions, and data and so forth that are necessary for processing of the programs (this is not limited to the external storage device, and programs may be stored in ROM that is a read-only storage device, for example). Data and so forth obtained by processing of the programs is stored in the RAM and the external storage device and so forth as appropriate.

In the hardware entity, the programs stored in the external storage device (or ROM or the like) and data necessary for processing of the programs are read into memory as necessary, and subjected to interpreting processing by the CPU as appropriate. As a result, the CPU realizes predetermined functions (the components described above as so-and-so unit, so-and-so means, and so forth).

The present invention is not limited to the above-described embodiments, and modifications can be made as appropriate without departing from the essence of the present invention. Processing described in the above embodiments is not restricted to being executed in the order of the time sequence described therein, and may be executed in parallel or individually, in accordance with the processing capabilities of the device executing processing, or as necessary.

In a case of realizing the processing functions at the hardware entity (device of the present invention) described in the above embodiments by a computer, the contents of processing for the function which the hardware entity should have are described by a program, as mentioned earlier. Executing this program on a computer realizes the processing functions of the above hardware entity on the computer.

The program describing these contents of processing can be recorded in a computer-readable recording medium. Any computer-readable recording medium may be used, such as magnetic recording devices, optical discs, opto-magnetic recording media, semiconductor memory, and so forth, for example. Specifically, examples of a magnetic recording device that can be used include hard disk devices, flexible disks, magnetic tape, and so forth. Examples of optical discs that can be used include DVD (Digital Versatile Disc), DVD-RAM (Random Access Memory), CD-ROM (Compact Disc Read Only Memory), CD-R (Recordable)/RW (ReWritable), and so forth, examples of opto-magnetic recording media that can be used include MO (Magneto-Optical disc) and so forth, and examples of semiconductor memory that can be used include EEP-ROM (Electronically Erasable and Programmable-Read Only Memory) and so forth.

Distribution of this program is performed by sales, transfer, lending, and so forth of a transportable recording medium such as a DVD, CD-ROM, or the like, in which the program is recorded, for example. Further, a configuration for distribution of the program may be made by storing the program in a storage device of a server computer, and transferring the program from the server computer to other computers via a network.

A computer that executes such a program first stores the program recorded in a transportable recording medium or the program transferred from a server computer in its own storage device to begin with, for example. Then, at the time of executing the processing, the computer reads the program stored in its own recording medium, and executes processing following the program that has been read out. As a separate form of executing the program, the computer may directly read the program from the transportable recording medium and execute processing following the program. Further, each time the program is transferred from the server computer to this computer, the computer may successively execute processing following the program that has been received. Also, a configuration may be made where the above-described processing is executed by a so-called ASP (Application Service Provider) type service, where the program is not transferred from the server computer to this computer, and the processing functions are realized just by the instructions for execution and the acquisition of results. Note that the program according to this form includes information provided to be used for processing by electronic computers that is equivalent to programs (data or the like that is not direct instructions to a computer but has a nature of defining processing of the computer).

Also, in this form, the hardware entity is configured by executing a predetermined program on a computer, but at least part of these contents of processing may be realized by hardware.

The invention claimed is:

1. A skill information presenting device comprising a processor configured to:
   acquire, from a first sensor attached to plate-shaped equipment, equipment behavior information indicating behavior of the plate-shaped equipment;
   acquire, from second sensors attached to insoles of boots used with the plate-shaped equipment, bodily behavior information indicating behavior of a body of an exerciser, the second sensors distinct from the first sensor; and
   calculate, from the equipment behavior information and the bodily behavior information, skill information, wherein the skill information indicates a skill relating to a turn in a physical exercise performed by the exerciser using the plate-shaped equipment and the boots, the skill information includes:
      a first skill indicator that includes information indicating behavior of the plate-shaped equipment at a start-of-turn time, a middle-of-turn time, and an end-of-turn time, and
      a second skill indicator that includes information indicating behavior of the body of the exerciser at the start-of-turn time, the middle-of-turn time, and the end-of-turn time,
   wherein the equipment behavior information includes time sequence information regarding angular velocity relating to a travel direction of the plate-shaped equipment and angular velocity relating to an edging direction of the plate-shaped equipment, and
   wherein the bodily behavior information includes time sequence information of pressure at each region of a sole of a right foot of the exerciser and pressure at each region of a sole of a left foot of the exerciser; and
   present the skill information, wherein presenting the skill information comprises visually presenting on a display, the skill information as a diagram illustrating a temporal change of the behavior of the plate-shaped equipment according to the first skill information aligned with a temporal change of pressure in respective regions of the two soles of the feet of the exerciser according to the second skill information in a segment from the start-of-turn time to the end-of-turn time of the turn.

2. The skill information presenting device according to claim 1, wherein the processor is further configured to:
   record sound data of mutually different frequencies or tones, assigned to the angular velocity relating to the travel direction of the plate-shaped equipment and the angular velocity relating to the edging direction of the plate-shaped equipment, and record sound data of mutually different frequencies or tones, assigned to each region of the sole of the right foot of the exerciser and each region of the sole of the left foot of the exerciser,
   wherein presenting the skill information further comprises auditorily presenting the skill information comprising:
      outputting the first skill indicator by using the time sequence information of the two angular velocities to identify a sound to generate out of sound data assigned to the two angular velocities, and sequentially generating the identified sound, and
      outputting the second skill indicator by using the time sequence information of pressure at each region of the two soles of the feet to identify a sound to generate out of sound data assigned to the regions, and sequentially generating the identified sound.

3. The skill information presenting device according to claim 2,
   wherein the processor is further configured to record:
      first target time sequence information that is time sequence information of angular velocity relating to travel direction of the plate-shaped equipment in an ideal turn,
      second target time sequence information that is time sequence information of angular velocity relating to edging direction of the plate-shaped equipment in the ideal turn, and
      third target time sequence information that is time sequence information of pressure at each region of the two soles of the feet in the ideal turn, and wherein auditorily presenting the skill information further comprises:
   identifying the sounds to generate on the basis of difference among:
      time sequence information of difference between the first target time sequence information and the time sequence information of the angular velocity relating to the travel direction of the plate-shaped equipment,
      time sequence information of difference between the second target time sequence information and the time sequence information of the angular velocity relating to the edging direction of the plate-shaped equipment, and
      time sequence information of difference between the third target time sequence information and the time sequence information of the pressure at each region of the two soles of the feet, and sequentially generating the identified sounds-data, in a manner where the smaller the difference, the smaller a volume of the identified sounds-data generated.

4. The skill information presenting device according to claim 1, wherein the processor is further configured to visually present on the display:

the first skill indicator as a diagram illustrating temporal change of the two angular velocities in a segment from the start-of-turn time to the end-of-turn time, for each turn, and the second skill indicator as a diagram illustrating temporal change of pressure in each region of the two soles of the feet in the segment from the start-of-turn time to the end-of-turn time, for each turn.

5. The skill information presenting device according to claim 1, wherein the processor is further configured to visually present on the display, the second skill indicator as a diagram illustrating temporal change of a region with a highest pressure out of the regions of the two soles of the feet in a segment from the start-of-turn time to the end-of-turn time, for each turn.

6. The skill information presenting device according to claim 1, wherein the processor is further configured to visually present on the display, the first skill indicator as a diagram illustrating the two angular velocities superimposed on a diagram representing a path of the turn, wherein, with regard to the angular velocity relating to the travel direction of the plate-shaped equipment, an orientation of the plate-shaped equipment relative to the travel direction of the plate-shaped equipment calculated from this angular velocity is presented as an angle of the plate-shaped equipment as to the path, and wherein, with regard to the angular velocity relating to the edging direction of the plate-shaped equipment, an inclination of the plate-shaped equipment as to a face of contact with the plate-shaped equipment calculated from this angular velocity is presented in color.

7. The skill information presenting device according to claim 1, wherein the bodily behavior information further includes time sequence information of:
a center-of-gravity position of the right foot of the exerciser and a center-of-gravity position of the left foot of the exerciser, and wherein visually presenting the skill information on the display further comprises presenting the second skill indicator as a diagram or video showing temporal change in the two center-of-gravity positions.

8. A skill information presenting method, comprising:
acquiring, using a first sensor attached to plate-shaped equipment, equipment behavior information indicating behavior of the plate-shaped equipment;
acquiring, using second sensors attached to insoles of boots used with the plate-shaped equipment, bodily behavior information indicating behavior of a body of an exerciser, the second sensors distinct from the first sensor; and
calculating skill information from the equipment behavior information and the bodily behavior information, wherein the skill information indicates a skill relating to a turn in a physical exercise performed by the exerciser using the plate-shaped equipment and the boots, the skill information includes:

a first skill indicator that includes information indicating behavior of the plate-shaped equipment at a start-of-turn time, a middle-of-turn time, and an end-of-turn time, and a second skill indicator that includes information indicating behavior of the body of the exerciser at the start-of-turn time, the middle-of-turn time, and the end-of-turn time, wherein the equipment behavior information includes time sequence information regarding angular velocity relating to a travel direction of the plate-shaped equipment and angular velocity relating to an edging direction of the plate-shaped equipment, and wherein the bodily behavior information includes time sequence information of pressure at each region of a sole of a right foot of the exerciser and pressure at each region of a sole of a left foot of the exerciser; and present the skill information, wherein presenting the skill information comprises visually presenting on a display, the skill information as a diagram illustrating a temporal change of the behavior of the plate-shaped equipment according to the first skill information aligned with a temporal change of pressure in respective regions of the two soles of the feet of the exerciser according to the second skill information in a segment from the start-of-turn time to the end-of-turn time of the turn.

9. The skill information presenting method according to claim 8, further comprising:

recording sound data of mutually different frequencies or tones, assigned to the angular velocity relating to the travel direction of the plate-shaped equipment and the angular velocity relating to the edging direction of the plate-shaped equipment, and recording sound data of mutually different frequencies or tones assigned to each region of the sole of the right foot of the exerciser and each region of the sole of the left foot of the exerciser, wherein presenting the skill information further comprises auditorily presenting the skill information comprising:

presenting the first skill information by using the time sequence information of the two angular velocities to identify a sound to generate out of sound data assigned to the two angular velocities, and sequentially generating the identified sound, and presenting the second indicator by using the time sequence information of pressure at each region of the two soles of the feet to identify a sound to generate out of sound data assigned to the regions, and sequentially generating the identified sound.

10. The skill information presenting method according to claim 9, further comprising:

recording first target time sequence information that is time sequence information of angular velocity relating to travel direction of the plate-shaped equipment in an ideal turn, recording second target time sequence information that is time sequence information of angular velocity relating to edging direction of the plate-shaped equipment in the ideal turn, and recording third target time sequence information that is time sequence information of pressure at each region of the two soles of the feet in the ideal turn, wherein auditorily presenting the skill information further comprises:

identifying the sounds to generate on the basis of difference among:
   time sequence information of difference between the first target time sequence information and the time sequence information of the angular velocity relating to the travel direction of the plate-shaped equipment,
   time sequence information of difference between the second target time sequence information and the time sequence information of the angular velocity relating to the edging direction of the plate-shaped equipment, and
   time sequence information of difference between the third target time sequence information and the time sequence information of the pressure at each region of the two soles of the feet, and
   sequentially generating the identified sounds, in a manner where the smaller the difference, the smaller the volume of the identified sounds generated.

11. The skill information presenting method according to claim 8, wherein visually presenting on the display the skill information further comprises:
   presenting the first skill indicator as a diagram illustrating temporal change of the two angular velocities in a segment from the start-of-turn time to the end-of-turn time, for each turn, and
   presenting the second skill indicator as a diagram illustrating temporal change of pressure in each region of the two soles of the feet in the segment from the start-of-turn time to the end-of-turn time, for each turn.

12. The skill information presenting method according to claim 8, wherein visually presenting on the display the skill information further comprises presenting the second skill indicator as a diagram illustrating temporal change of a region with a highest pressure out of the regions of the two soles of the feet in a segment from the start-of-turn time to the end-of-turn time, for each turn.

13. The skill information presenting method according to claim 8, wherein visually presenting on the display the skill information further comprises presenting the first skill indicator as a diagram illustrating the two angular velocities superimposed on a diagram representing a path of the turn,
   wherein, with regard to the angular velocity relating to the travel direction of the plate- shaped equipment, an orientation of the plate-shaped equipment relative to the travel direction of the plate-shaped equipment calculated from this angular velocity is presented as an angle of the plate-shaped equipment as to the path, and
   wherein, with regard to the angular velocity relating to the edging direction of the plate- shaped equipment, an inclination of the plate-shaped equipment as to a face of contact with the plate-shaped equipment calculated from this angular velocity is presented in color.

14. The skill information presenting method according to claim 8, wherein the bodily behavior information further includes time sequence information of: a center-of-gravity position of the right foot of the exerciser and a center-of-gravity position of the left foot of the exerciser, and
   wherein visually presenting the skill information on the display further comprises presenting the second skill indicator as a diagram or video showing temporal change in the two center-of-gravity positions.

15. A system for presenting skill information, comprising:
a processor; and
a memory storing computer-executable program instructions that when executed by the processor cause the processor to:
   acquire, from a first sensor attached to plate-shaped equipment, equipment behavior information indicating behavior of the plate-shaped equipment;
   -acquire, from second sensors attached to insoles of boots used with the plate-shaped equipment, bodily behavior information indicating behavior of a body of an exerciser, the second sensors distinct from the first sensor;
   calculate, from the equipment behavior information and the bodily behavior information, skill information, wherein the skill information indicates a skill relating to a turn in a physical exercise performed by the exerciser using the plate-shaped equipment and the boots, the skill information includes:
      a first skill indicator that includes information indicating behavior of the plate- shaped equipment at a start-of-turn time, a middle-of-turn time, and an end-of-turn time, and
      a second skill indicator that includes information indicating behavior of the body of the exerciser at the start-of-turn time, the middle-of-turn time, and the end-of-turn time,
      wherein the equipment behavior information includes time sequence information regarding angular velocity relating to a travel direction of the plate-shaped equipment and angular velocity relating to an edging direction of the plate-shaped equipment, and
      wherein the bodily behavior information includes time sequence information of pressure at each region of a sole of a right foot of the exerciser and pressure at each region of a sole of a left foot of the exerciser; and
   present the skill information, wherein presenting the skill information comprises visually presenting on a display, the skill information as a diagram illustrating a temporal change of the behavior of the plate-shaped equipment according to the first skill information aligned with a temporal change of pressure in respective regions of the two soles of the feet of the exerciser according to the second skill information in a segment from the start-of-turn time to the end-of-turn time of the turn.

16. The system of claim 15, wherein the computer-executable program instructions further cause the processor to:
   record sound data of mutually different frequencies or tones, assigned to the angular velocity relating to the travel direction of the plate-shaped equipment and the angular velocity relating to the edging direction of the plate-shaped equipment, and record sound data of mutually different frequencies or tones assigned to each region of the sole of the right foot of the exerciser and each region of the sole of the left foot of the exerciser,
   wherein presenting the skill information further comprises auditorily presenting the skill information comprising:
      presenting the first skill indicator by using the time sequence information of the two angular velocities to identify a sound to generate out of sound data assigned to the two angular velocities, and sequentially generating the identified sound, and
      presenting the first skill indicator by using the time sequence information of pressure at each region of the two soles of the feet to identify a sound to generate out of sound data assigned to the regions, and sequentially generating the identified sound.

17. The system of claim 16, wherein the computer-executable program instructions further cause the processor to:
- record first target time sequence information that is time sequence information of angular velocity relating to travel direction of the plate-shaped equipment in an ideal turn,
- record second target time sequence information that is time sequence information of angular velocity relating to edging direction of the plate-shaped equipment in the ideal turn, and
- record third target time sequence information that is time sequence information of pressure at each region of the two soles of the feet in the ideal turn, and wherein auditorily presenting the skill information further comprises:

identifying the sounds to generate on the basis of difference among:
- time sequence information of difference between the first target time sequence information and the time sequence information of the angular velocity relating to the travel direction of the plate-shaped equipment,
- time sequence information of difference between the second target time sequence information and the time sequence information of the angular velocity relating to the edging direction of the plate-shaped equipment, and
- time sequence information of difference between the third target time sequence information and the time sequence information of the pressure at each region of the two soles of the feet, and sequentially generating the identified sounds, in a manner where the smaller the difference, the smaller the volume of the identified sounds generated.

18. The system of claim 15, wherein the computer-executable program instructions further cause the processor to visually present on the display:
- the first skill indicator as a diagram illustrating temporal change of the two angular velocities in a segment from the start-of-turn time to the end-of-turn time, for each turn, and
- the second skill indicator as a diagram illustrating temporal change of pressure in each region of the two soles of the feet in the segment from the start-of-turn time to the end-of-turn time, for each turn.

19. The system of claim 15, wherein the computer-executable program instructions further cause the processor to visually present on the display, the second skill indicator as a diagram illustrating temporal change of a region with a highest pressure out of the regions of the two soles of the feet in a segment from the start-of-turn time to the end-of-turn time, for each turn.

20. The system of claim 15, wherein the computer-executable program instructions further cause the processor to visually present on the display, the first skill indicator as a diagram illustrating the two angular velocities superimposed on a diagram representing a path of the turn,
- wherein, with regard to the angular velocity relating to the travel direction of the plate-shaped equipment, an orientation of the plate-shaped equipment relative to the travel direction of the plate-shaped equipment calculated from this angular velocity is presented as an angle of the plate-shaped equipment as to the path, and
- wherein, with regard to the angular velocity relating to the edging direction of the plate-shaped equipment, an inclination of the plate-shaped equipment as to a face of contact with the plate-shaped equipment calculated from this angular velocity is presented in color.

* * * * *